US006147039A

United States Patent [19]

Jacques et al.

[11] Patent Number: 6,147,039

[45] **Date of Patent: *Nov. 14, 2000**

[54] ANTIBACTERIAL LIQUID HAND CLEANING COMPOSITIONS CONTAINING A HYDROXY CONTAINING ORGANIC ACID

[75] Inventors: Anne Jacques, Oupeye; Isabelle Leonard, Mont-Sur-Marchiennes, both of Belgium

[73] Assignee: Colgate-Palmolive Company, New York, N.Y.

[ * ] Notice: This patent is subject to a terminal disclaimer.

[21] Appl. No.: 09/461,610

[22] Filed: Dec. 15, 1999

Related U.S. Application Data

[63] Continuation of application No. 09/304,158, Apr. 30, 1999, abandoned.

[51] Int. Cl.[7] .......................................... A61K 7/50

[52] U.S. Cl. .......................... 510/138; 510/130; 510/137; 510/428; 510/490

[58] Field of Search .................................... 510/130, 129, 510/424, 428, 137, 138, 490

[56] References Cited

U.S. PATENT DOCUMENTS 5,681,802 10/1997 Fujiwara et al. ........................ 510/530

*Primary Examiner*—Necholus Ogden
*Attorney, Agent, or Firm*—Richard E. Nanfeldt

[57] ABSTRACT

An antibacterial liquid hand cleaning composition with desirable cleansing properties to the human skin comprising a $C_{8-18}$ ethoxylated alkyl ether sulfate anionic surfactant, a betaine surfactant, a hydroxy containing organic acid and water.

2 Claims, No Drawings

ANTIBACTERIAL LIQUID HAND CLEANING COMPOSITIONS CONTAINING A HYDROXY CONTAINING ORGANIC ACID

This is a continuation of pending prior application Ser. No. 9/304,158 filed Apr. 30, 1990, now abandoned which application is now pending and is incorporated herein by reference.

FIELD OF INVENTION

This invention relates to an antibacterial liquid hand cleaning composition which imparts mildness to the skin which is designed in particular for cleaning the skin of the body and which is effective in removing both particular and grease soil.

BACKGROUND OF THE INVENTION

Liquid personal cleaning compositions are well known in the art such as U.S. Pat. Nos. 4,387,040; 4,673,523; 3,697,644; 3,932,610; 4,031,306; 4,061,602; 4,387,040; 4,917,823; 5,296,158; 4,338,211; 4,190,549 and 4,861,507.

SUMMARY OF THE INVENTION

It has now been found that an antibacterial liquid hand cleaning composition can be formulated with an anionic surfactant and zwitterionic which has desirable cleaning properties, mildness to the human skin.

An object of this invention is to provide an antibacterial liquid hand cleaning composition comprises a sulfate and/or sulfonate anionic surfactant, a zwitterionic surfactant and a hydroxy aliphatic acid, wherein the composition does not contain any silicas, abrasives, phosphoric acid, phosphonic acid, boric acid, alkali metal carbonates, alkaline earth metal carbonates, alkyl glycine surfactant, cyclic imidinium surfactant, or more than 3 wt. % of a fatty acid or salt thereof.

Another object of this invention is to provide an antibacterial liquid hand cleaning composition with desirable high foaming and cleaning properties which kills bacteria.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

DETAILED DESCRIPTION OF THE INVENTION

The present invention relates to an antibacterial liquid hand soap comprising approximately by weight:

(a) 0.25% to 5%, more preferably 0.5% to 4% of a zwitterionic surfactant;

(b) 5% to 16%, more preferably 6% to 15% of at least one second surfactant selected from the group consisting of anionic sulfate surfactants, anionic sulfonate surfactants, alkyl polyglucosides, amine oxides surfactants, glucamide surfactants and an alkali metal fatty acid soap surfactant having 8 to 18 carbon atoms and mixtures thereof wherein anionic surfactants are preferred;

(c) 0 to 2%, more preferably 0.1% to 2% of a polymer thickener such as xanthan gum, methoacrylate polymeric thickener, and a hydroxy alkyl cellulose thicker;

(d) 0.1% to 4%, more preferably 0.2% to 3% of a hydroxy containing organic acid selected from the group consisting of ortho hydroxy benzoic acid, lactic acid and citric acid and mixtures thereof wherein the composition has a pH of 3 to 4 and has a viscosity of 100 to 100,000 cps, more preferably 1,000 to 60,000 cps at 25° C. using a TD spindle at 5 rpm as measured on a Brookfield RUTDV-11 viscometer, wherein the composition does not contain any grease release agents such as choline chloride or buffering system which is a nitrogenous buffer which is ammonium or alkaline earth carbonate, guanidine derivates, alkoxylalkyl amines and alkyleneamines $C_3$–$C_7$ alkyl and alkenyl monobasic and dibasic acids such as $C_4$–$C_7$ aliphatic carboxylic diacids which do not contain a hydroxy group, boric acid, phosphoric acid, amino alkylene phosphonic acid and the composition is pourable and not a gel has a complex viscosity at 1 rads$^{-1}$ of less than 0.4 Pascal seconds.

The anionic sulfonate surfactants which may be used in the detergent of this invention are water soluble and include the sodium, potassium, ammonium and ethanolammonium salts of linear $C_8$–$C_{16}$ alkyl benzene sulfonates; $C_{10}$–$C_{20}$ paraffin sulfonates, alpha olefin sulfonates containing about 10–24 carbon atoms and $C_8$–$C_{18}$ alkyl sulfates and mixtures thereof. The preferred anionic sulfonate surfactant is a $C_{12-18}$ paraffin sulfonate.

The paraffin sulfonates may be monosulfonates or di-sulfonates and usually are mixtures thereof, obtained by sulfonating paraffins of 10 to 20 carbon atoms. Preferred paraffin sulfonates are those of $C_{12-18}$ carbon atoms chains, and more preferably they are of $C_{14-17}$ chains. Paraffin sulfonates that have the sulfonate group(s) distributed along the paraffin chain are described in U.S. Pat. Nos. 2,503,280; 2,507,088; 3,260,744; and 3,372,188; and also in German Patent 735,096. Such compounds may be made to specifications and desirably the content of paraffin sulfonates outside the $C_{14-17}$ range will be minor and will be minimized, as will be any contents of di- or poly-sulfonates.

Examples of suitable other sulfonated anionic detergents are the well known higher alkyl mononuclear aromatic sulfonates, such as the higher alkylbenzene sulfonates containing 9 to 18 or preferably 9 to 16 carbon atoms in the higher alkyl group in a straight or branched chain, or $C_{8-15}$ alkyl toluene sulfonates. A preferred alkylbenzene sulfonate is a linear alkylbenzene sulfonate having a higher content of 3-phenyl (or higher) isomers and a correspondingly lower content (well below 50%) of 2-phenyl (or lower) isomers, such as those sulfonates wherein the benzene ring is attached mostly at the 3 or higher (for example 4, 5, 6 or 7) position of the alkyl group and the content of the isomers in which the benzene ring is attached in the 2 or 1 position is correspondingly low. Preferred materials are set forth in U.S. Pat. No. 3,320,174, especially those in which the alkyls are of 10 to 13 carbon atoms.

The $C_{8-18}$ ethoxylated alkyl ether sulfate surfactants have the structure $$R\text{-}(OCHCH_2)_nOSO^-_3M^+$$

wherein n is about 1 to about 22 more preferably 1 to 3 and R is an alkyl group having about 8 to about 18 carbon atoms, more preferably 12 to 15 and natural cuts, for example, $C_{12-14}$ or $C_{12-16}$ and M is an ammonium cation or a metal cation, most preferably sodium.

The ethoxylated alkyl ether sulfate may be made by sulfating the condensation product of ethylene oxide and $C_{8-10}$ alkanol, and neutralizing the resultant product. The ethoxylated alkyl ether sulfates differ from one another in the number of carbon atoms in the alcohols and in the number of moles of ethylene oxide reacted with one mole of such alcohol. Preferred ethoxylated alkyl ether polyethenoxy sulfates contain 12 to 15 carbon atoms in the alcohols and in the alkyl groups thereof, e.g., sodium myristyl (3 EO) sulfate.

Ethoxylated $C_{8-18}$ alkylphenyl ether sulfates containing from 2 to 6 moles of ethylene oxide in the molecule are also suitable for use in the invention compositions. These detergents can be prepared by reacting an alkyl phenol with 2 to 6 moles of ethylene oxide and sulfating and neutralizing the resultant ethoxylated alkylphenol. The concentration of the ethoxylated alkyl ether sulfate surfactant is about 1 to about 8 wt. %.

Other example of operative anionic surfactants includes sodium dioctyl sulfosuccinate [di-(2 ethylhexyl) sodium sulfosuccinate being one] and corresponding dihexyl and dioctyl esters. The preferred sulfosuccinic acid ester salts are esters of aliphitic alcohols such as saturated alkanols of 4 to 12 carbon atoms and are normally diesters of such alkanols. More preferably such are alkali metal salts of the diesters of alcohols of 6 to 10 carbons atoms and more preferably the diesters will be from octanol, such as 2-ethyl hexanol, and the sulfonic acid salt will be the sodium salt.

The water soluble aliphatic ethoxylated nonionic surfactants which can be utilized in this invention are commercially well known and include the primary aliphatic alcohol ethoxylates and secondary aliphatic alcohol ethoxylates. The length of the polyethenoxy chain can be adjusted to achieve the desired balance between the hydrophobic and hydrophilic elements.

The nonionic surfactant class includes the condensation products of a higher alcohol (e.g., an alkanol containing about 8 to 16 carbon atoms in a straight or branched chain configuration) condensed with about 4 to 20 moles of ethylene oxide, for example, lauryl or myristyl alcohol condensed with about 16 moles of ethylene oxide (EO), tridecanol condensed with about 6 to 15 moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to about 14 carbon atoms in length and wherein the condensate contains either about 6 moles of EO per mole of total alcohol or about 9 moles of EO per mole of alcohol and tallow alcohol ethoxylates containing 6 EO to 11 EO per mole of alcohol.

A preferred group of the foregoing nonionic surfactants are the Neodol ethoxylates (Shell Co.), which are higher aliphatic, primary alcohol containing about 9–15-carbon atoms, such as $C_9$–$C_{11}$ alkanol condensed with 4 to 10 moles of ethylene oxide (Neodol 91-8 or Neodol 91-5), $C_{12-13}$ alkanol condensed with 6.5 moles ethylene oxide (Neodol 23-6.5), $C_{12-15}$ alkanol condensed with 12 moles ethylene oxide (Neodol 25-12), $C_{14-15}$ alkanol condensed with 13 moles ethylene oxide (Neodol 45-13), and the like. Such ethoxamers have an HLB (hydrophobic lipophilic balance) value of about 8 to 15 and give good O/W emulsification, whereas ethoxamers with HLB values below 7 contain less than 4 ethyleneoxide groups and tend to be poor emulsifiers and poor detergents.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are $C_{11}$–$C_{15}$ secondary alkanol condensed with either 9 EO (Tergitol 15-S-9) or 12 EO (Tergitol 15-S-12) marketed by Union Carbide.

The amine oxides are semi-polar nonionic surfactants which comprise compounds and mixtures of compounds having the formula

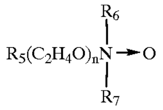

wherein $R_5$ is an alkyl, 2-hydroxyalkyl, 3-hydroxyalkyl, or 3-alkoxy-2-hydroxypropyl radical in which the alkyl and alkoxy, respectively, contain from 8 to 18 carbon atoms, $R_6$ and $R_7$ are each methyl, ethyl, propyl, isopropyl, 2-hydroxyethyl, 2-hydroxypropyl, or 3-hydroxypropyl, and n is from 0 to 10. Particularly preferred are amine oxides of the formula:

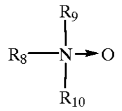

wherein $R_8$ is a $C_{12-16}$ alkyl group or amido radical:

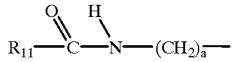

wherein $R_{11}$ is an alkyl group having about 9 to 19 carbon atoms and a is an integer 1 to 4 and $R_9$ and $R_{10}$ are methyl or ethyl. The above ethylene oxide condensates, amides, and amine oxides are more fully described in U.S. Pat. No. 4,316,824 which is hereby incorporated herein by reference. An especially preferred amine oxide is cocoamido propyl dimethyl amine oxide.

The water-soluble zwitterionic surfactant, which is an essential ingredient of present liquid detergent composition, provides good foaming properties and mildness to the present nonionic based liquid detergent. The zwitterionic surfactant is a water soluble betaine having the general formula:

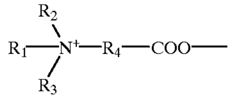

wherein $R_1$ is an alkyl group having 10 to 20 carbon atoms, preferably 12 to 16 carbon atoms, or the amido radical:

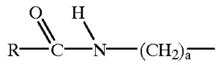

wherein R is an alkyl group having 9 to 19 carbon atoms and a is the integer 1 to 4; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl dimethyl betaine or 2-(N-decyl-N, N-dimethyl-ammonia) acetate, coco dimethyl betaine or 2-(N-coco N, N-dimethylammonio) acetate, myristyl dimethyl betaine, palmityl dimethyl betaine, lauryl diemethyl betaine, cetyl dimethyl betaine, stearyl dimethyl betaine, etc. The amidobetaines similarly include cocoamidoethylbetaine, cocoamidopropyl betaine and the like. A preferred betaine is coco ($C_8$–$C_{18}$) amidopropyl dimethyl betaine.

Amine oxide semi-polar nonionic surfactants comprise compounds and mixtures of compounds having the formula

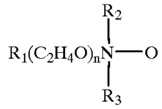

wherein $R_1$ is an alkyl, 2-hydroxyalkyl, 3-hydroxyalkyl, or 3-alkoxy-2-hydroxypropyl radical in which the alkyl and alkoxy, respectively, contain from 8 to 18 carbon atoms, $R_2$ and $R_3$ are each methyl, ethyl, propyl, isopropyl, 2-hydroxyethyl, 2-hydroxypropyl, or 3-hydroxypropyl, and n is from 0 to 10. Particularly preferred are amine oxides of the formula:

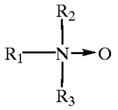

wherein $R_1$ is a $C_{12-16}$ alkyl and $R_2$ and $R_3$ are methyl or ethyl. The above ethylene oxide condensates, amides, and amine oxides are more fully described in U.S. Pat. No. 4,316,824 which is hereby incorporated herein by reference.

The alkyl polysaccharides surfactants, which can be used in conjunction have a hydrophobic group containing from about 8 to about 20 carbon atoms, preferably from about 10 to about 16 carbon atoms, most preferably from about 12 to about 14 carbon atoms, and polysaccharide hydrophilic group containing from about 1.5 to about 10, preferably from about 1.5 to about 4, most preferably from about 1.6 to about 2.7 saccharide units (e.g., galactoside, glucoside, fructoside, glucosyl, fructosyl; and/or galactosyl units). Mixtures of saccharide moieties may be used in the alkyl polysaccharide surfactants. The number x indicates the number of saccharide units in a particular alkyl polysaccharide surfactant. For a particular alkyl polysaccharide molecule x can only assume integral values. In any physical sample of alkyl polysaccharide surfactants there will be in general molecules having different x values. The physical sample can be characterized by the average value of x and this average value can assume non-integral values. In this specification the values of x are to be understood to be average values. The hydrophobic group (R) can be attached at the 2-, 3-, or 4-positions rather than at the 1-position, (thus giving e.g. a glucosyl or galactosyl as opposed to a glucoside or galactoside). However, attachment through the 1-position, i.e., glucosides, galactoside, fructosides, etc., is preferred. In the preferred product the additional saccharide units are predominately attached to the previous saccharide unit's 2-position. Attachment through the 3-, 4-, and 6-positions can also occur. Optionally and less desirably there can be a polyalkoxide chain joining the hydrophobic moiety (R) and the polysaccharide chain. The preferred alkoxide moiety is ethoxide.

Typical hydrophobic groups include alkyl groups, either saturated or unsaturated, branched or unbranched containing from about 8 to about 20, preferably from about 10 to about 18 carbon atoms. Preferably, the alkyl group is a straight chain saturated alkyl group. The alkyl group can contain up to 3 hydroxy groups and/or the polyalkoxide chain can contain up to about 30, preferably less than about 10, alkoxide moieties.

Suitable alkyl polysaccharides are decyl, dodecyl, tetradecyl, pentadecyl, hexadecyl, and octadecyl, di-, tri-, tetra-, penta-, and hexaglucosides, galactosides, lactosides, fructosides, fructosyls, lactosyls, glucosyls and/or galactosyls and mixtures thereof.

The alkyl monosaccharides are relatively less soluble in water than the higher alkyl polysaccharides. When used in admixture with alkyl polysaccharides, the alkyl monosaccharides are solubilized to some extent. The use of alkyl monosaccharides in admixture with alkyl polysaccharides is a preferred mode of carrying out the invention. Suitable mixtures include coconut alkyl, di-, tri-, tetra-, and pentaglucosides and tallow alkyl tetra-, penta-, and hexaglucosides.

The preferred alkyl polysaccharides are alkyl polyglucosides having the formula $$RO(C_nH_{2n}O)_r(Z)_x$$

wherein Z is derived from glucose, R is a hydrophobic group selected from the group consisting of alkyl, alkylphenyl, hydroxyalkylphenyl, and mixtures thereof in which said alkyl groups contain from about 10 to about 18, preferably from about 12 to about 14 carbon atoms; n is 2 or 3 preferably 2, r is from 0 to 10, preferable 0; and x is from 1.5 to 8, preferably from 1.5 to 4, most preferably from 1.6 to 2.7. To prepare these compounds a long chain alcohol ($R_2OH$) can be reacted with glucose, in the presence of an acid catalyst to form the desired glucoside. Alternatively the alkyl polyglucosides can be prepared by a two step procedure in which a short chain alcohol ($R_1OH$) can be reacted with glucose, in the presence of an acid catalyst to form the desired glucoside. Alternatively the alkyl polyglucosides can be prepared by a two step procedure in which a short chain alcohol ($C_{1-6}$) is reacted with glucose or a polyglucoside (x=2 to 4) to yield a short chain alkyl glucoside (x=1 to 4) which can in turn be reacted with a longer chain alcohol ($R_2OH$) to displace the short chain alcohol and obtain the desired alkyl polyglucoside. If this two step procedure is used, the short chain alkylglucosde content of the final alkyl polyglucoside material should be less than 50%, preferably less than 10%, more preferably less than about 5%, most preferably 0% of the alkyl polyglucoside.

The amount of unreacted alcohol (the free fatty alcohol content) in the desired alkyl polysaccharide surfactant is preferably less than about 2%, more preferably less than about 0.5% by weight of the total of the alkyl polysaccharide. For some uses it is desirable to have the alkyl monosaccharide content less than about 10%.

The used herein, "alkyl polysaccharide surfactant" is intended to represent both the preferred glucose and galactose derived surfactants and the less preferred alkyl polysaccharide surfactants. Throughout this specification, "alkyl polyglucoside" is used to include alkyl polyglycosides because the stereochemistry of the saccharide moiety is changed during the preparation reaction.

An especially preferred APG glycoside surfactant is Glucopon 625 AUP glycoside manufactured by the Henkel Corporation of Ambler, Pa. is a nonionic alkyl polyglycoside characterized by the formula:

$$C_nH_{2n}+1O(C_6H_{10}O_5)_xH$$

wherein n=10 (2%); n=122 (65%); n=14 (21–28%); n=16 (4–8%) and n=18 (0.5% and x (degree of polymerization)=

1.6. APG 625 has: a pH of 6 to 12 (10% of APG 625 in distilled water); a specific gravity at 25° C. of 1.1 g/ml; a density at 25° C. of 9.1 lbs/gallon; a calculated HLB of 12.1 and a Brookfield viscosity at 35° C., 21 spindle, 5–10 RPM of 3,000 to 7,000 cps.

The instant light duty liquid nonmicroemulsion compositions can contain about 0 wt. % to about 10 wt. %, more preferably about 1 wt. % to about 8 wt. %, of at least one solubilizing agent selected from the group consisting of a $C_{2-5}$ mono, dihydroxy or polyhydroxy alkanols such as ethanol, isopropanol, glycerol ethylene glycol, diethylene glycol and propylene glycol and mixtures thereof and alkali metal cumene or xylene sulfonates such as sodium cumene sulfonate and sodium xylene sulfonate. The solubilizing agents are included in order to control low temperature cloud clear properties. Urea can be optionally employed in the instant composition as a supplemental solubilizing agent at a concentration of 0 to about 10 wt. %, more preferably about 0.5 wt. % to about 8 wt. %.

The instant formulas explicitly exclude alkali metal silicates and alkali metal builders such as alkali metal polyphosphates, alkali metal carbonates, alkali metal phosphonates and alkali metal citrates because these materials, if used in the instant composition, would cause the composition to have a high pH as well as leaving residue on the surface being cleaned.

The final essential ingredient in the inventive compositions having improved interfacial tension properties is water. The proportion of water in the compositions generally is in the range of 10% to 95%.

The liquid cleaning composition of this invention may, if desired, also contain other components either to provide additional effect or to make the product more attractive to the consumer. The following are mentioned by way of example: Colors or dyes in amounts up to 0.5% by weight; bactericides in amounts up to 1% by weight; preservatives or antioxidizing agents, such as formalin, 5-bromo-5-nitro-dioxan-1,3; 5-chloro-2-methyl-4-isothaliazolin-3-one, 2,6-di-tert.butyl-p-cresol, etc., in amounts up to 2% by weight; and pH adjusting agents, such as sulfuric acid or sodium hydroxide, as needed. Furthermore, if opaque compositions are desired, up to 4% by weight of an opacifier may be added.

Polyethylene glycol can be optional used in the instant composition has a molecular weight of 200 to 1,000, wherein the polyethylene glycol has the structure $$HO(CH_2CH_2O)_nH$$

wherein n is 4 to 52. The concentration of the polyethylene glycol in the instant composition is 0 to 5 wt. %, more preferably 0.1 wt. % to 4 wt. %.

In final form, the instant compositions exhibit stability at reduced and increased temperatures. More specifically, such compositions remain clear and stable in the range of 5° C. to 50° C., especially 10° C. to 43° C. Such compositions exhibit a pH of 3 to 4. The liquid microemulsion compositions are readily pourable and exhibit a viscosity in the range of 6 to 300 milliPascal. second (mPas.) as measured at 25° C. with a Brookfield RVT Viscometer using a #1 spindle rotating at 20 RPM. Preferably, the viscosity is maintained in the range of 10 to 200 mPas.

The following examples illustrate the liquid body cleaning compositions of the described invention. Unless otherwise specified, all percentages are by weight. The exemplified compositions are illustrative only and do not limit the scope of the invention. Unless otherwise specified, the proportions in the examples and elsewhere in the specification are by weight.

EXAMPLE 1

The following compositions in wt. % were prepared by simple mixing procedure:

| | A | B | C | D |
|---|---|---|---|---|
| Cocoamido propyl dimethyl betaine | 1.44 | 1.44 | 1.44 | 1.44 |
| Sodium$C_{13-14}$AEOS2:1 EO | 8.12 | 8.12 | 8.12 | 8.12 |
| Latic acid | 2 | | | |
| Citric acid | | 2 | | |
| Ortho hydroxy benzoic acid | | | | 0.5 |
| Water | Bal. | Bal. | Bal. | Bal. |
| Appearance @ RT | clear | clear | clear | clear |
| Appearance @ 4C | clear | clear | clear | clear |
| pH | | | | |
| PrEN1040[1] | 3 | 2 | 0.9 | 5.8 |

[1]minute contact time against *S. Aureus* bacterial-value expressed in log of reduction after one minute of contact time at 25 C.

[1] 1 minute contact time against S. Aureus bacterial-value expressed in log of reduction after one minute of contact time at 25C.

EXAMPLE 2

The following formulas in wt. % were made and tested:

| | A | B | C | D |
|---|---|---|---|---|
| Water | 55.26 | 56.8 | 60.72 | 56.8 |
| Preservative | 0.2 | 0.2 | 0.2 | 0.2 |
| SLES Naturel | 30 | 30 | 30 | 30 |
| Cocoamido propyl betaine | 4.8 | 4.8 | 4.8 | 4.8 |
| Cheastnut leaves extract | 0.1 | 0.1 | 0.1 | 0.1 |
| Perfume Apollo | 0.3 | 0.3 | 0.3 | 0.3 |
| Citric Acid | 4 | | | |
| Lactic Acid | | 2.27 | | 2.27 |
| Ortho hydroxy benzoic acid | | | 0.51 | |
| Dye | 0.8 | 0.8 | 0.8 | 0.8 |
| NaOH | 2.5 | 2.83 | 0.2 | 1.23 |
| NaCl | 2 | 1.86 | 2.33 | 1.86 |
| Final pH | 4.01 | 3.98 | 4.02 | 3.5 |
| Contact time | 1 minute | 1 minute | 1 minute | 5 minutes |
| Log reduction | 2 against *S. Aureus* | 3 against *S. Aureus* | >5 against *S. Aureus* | >4 against *Ps. Aeruginosa* >5 against *S. Aureus* |

What is claimed:

1. An antibacterial liquid hand soap consisting essentially of approximately by weight:

(a) 0.5% to 4% of a zwitterionic surfactant;

(b) 5% to 16% of at least one second surfactant selected from the group consisting of anionic sulfate surfactants, anionic sulfonate surfactants, alkyl polyglucosides, amine oxides surfactants, and glucamide surfactants and mixtures thereof;

(c) 0.1% to 4% of ortho hydroxy benzoic acid; and (d) the balance being water, wherein the composition does not contain C3–C7 alkyl and alkenyl monobasic and dibasic acids which do not contain a hydroxy group.

2. The composition of claim 1, wherein the second surfactant is a sulfate anionic surfactant.

* * * * *